(12) United States Patent
Pennathur et al.

(10) Patent No.: US 11,638,539 B2
(45) Date of Patent: May 2, 2023

(54) NEEDLES FOR MEASUREMENT OF BODY FLUID ANALYTES SUCH AS GLUCOSE

(71) Applicant: LAXMI THERAPEUTIC DEVICES, INC., Goleta, CA (US)

(72) Inventors: Sumita Pennathur, Goleta, CA (US); Michelle Carrie Halpin, Santa Barbara, CA (US); Landon Christopher Peik, Santa Barbara, CA (US); Leanne Beer, San Francisco, CA (US); Bill Van Antwerp, Valencia, CA (US); Justin Daniel Rofeh, Beverly Hills, CA (US); Seth Boden, Goleta, CA (US); Luke Satish Kumar Theogarajan, Goleta, CA (US)

(73) Assignee: LAXMI THERAPEUTIC DEVICES, INC., Goleta, CA (US)

( * ) Notice: Subject to any disclaimer, the term of this patent is extended or adjusted under 35 U.S.C. 154(b) by 0 days.

(21) Appl. No.: 17/299,254

(22) PCT Filed: Dec. 3, 2019

(86) PCT No.: PCT/US2019/064215
§ 371 (c)(1),
(2) Date: Jun. 2, 2021

(87) PCT Pub. No.: WO2020/117788
PCT Pub. Date: Jun. 11, 2020

(65) Prior Publication Data
US 2022/0015668 A1    Jan. 20, 2022

Related U.S. Application Data

(60) Provisional application No. 62/774,505, filed on Dec. 3, 2018.

(51) Int. Cl.
*A61B 5/145* (2006.01)
*A61B 5/00* (2006.01)

(52) U.S. Cl.
CPC ...... *A61B 5/14503* (2013.01); *A61B 5/14532* (2013.01); *A61B 5/685* (2013.01); *A61B 2562/125* (2013.01)

(58) Field of Classification Search
CPC . A61B 5/14503; A61B 5/14532; A61B 5/685; A61B 2562/125; A61B 5/14865
See application file for complete search history.

(56) References Cited

U.S. PATENT DOCUMENTS

| 4,671,288 | A | | 6/1987 | Gough | |
|---|---|---|---|---|---|
| 5,165,407 | A | * | 11/1992 | Wilson | A61B 5/14865 204/403.11 |

(Continued)

FOREIGN PATENT DOCUMENTS

WO    WO 2018/065954 A1    4/2018

OTHER PUBLICATIONS

International Search Report and Written Opinion for Application No. PCT/US2019/064215, dated Feb. 10, 2020, 10 pages.

(Continued)

*Primary Examiner* — Eric J Messersmith
(74) *Attorney, Agent, or Firm* — Lewis Roca Rothgerber Christie LLP

(57) ABSTRACT

Microneedles for analysis of analytes in body fluids may be manufactured from robust materials such as stainless steel by laser cutting at least the basic needle configuration, applying a coating to electrically insulate and/or assure biocompatibility of the needle, and forming electrodes on the needles via lithography or other processes (preferably after treatment of the coated areas at which the electrodes are to be applied). Preferably, the needles have a depression (Continued)

formed therein from which the electrodes extend, and which contains a sensing medium which produces a measurable output in response to the local concentration of the analyte of interest Thus, when a needle is inserted into the skin such that the depression and its sensing medium encounters body fluids, analyte measurements can be obtained via the electrodes.

20 Claims, 5 Drawing Sheets

(56) References Cited

U.S. PATENT DOCUMENTS

| | | | | |
|---|---|---|---|---|
| 2002/0168290 | A1* | 11/2002 | Yuzhakov | A61B 5/14532 |
| | | | | 600/583 |
| 2010/0069792 | A1* | 3/2010 | Fujimura | A61B 5/15117 |
| | | | | 600/583 |
| 2010/0130886 | A1 | 5/2010 | Kaneto et al. | |
| 2010/0331729 | A1 | 12/2010 | Naito et al. | |
| 2011/0071377 | A1 | 3/2011 | Kaneto et al. | |
| 2011/0218490 | A1 | 9/2011 | Ocvirk et al. | |
| 2014/0142405 | A1 | 5/2014 | Brister et al. | |
| 2014/0213866 | A1* | 7/2014 | Simpson | A61B 17/3468 |
| | | | | 600/345 |
| 2016/0235346 | A1 | 4/2016 | Liu et al. | |
| 2016/0157766 | A1* | 6/2016 | Simpson | A61B 5/6843 |
| | | | | 600/345 |
| 2017/0181672 | A1 | 6/2017 | Nogueira et al. | |
| 2018/0057851 | A1* | 3/2018 | Fukuda | C12Q 1/006 |
| 2018/0368712 | A1* | 12/2018 | Gardner | C23C 16/325 |

OTHER PUBLICATIONS

Vasylieva et al., "Silicon/SU8 multi-electrode micro-needle for in vivo neurochemical monitoring," Biosensors and Bioelectronics, vol. 72, pp. 148-155, 2015.

Extended European Search Report for Application No. 19892785.7, dated Jul. 25, 2022, 9 pages.

* cited by examiner

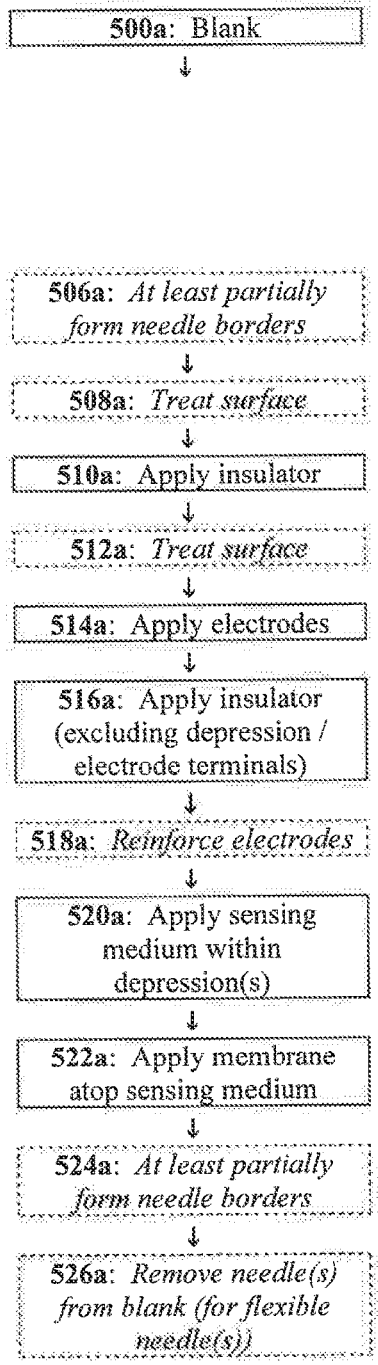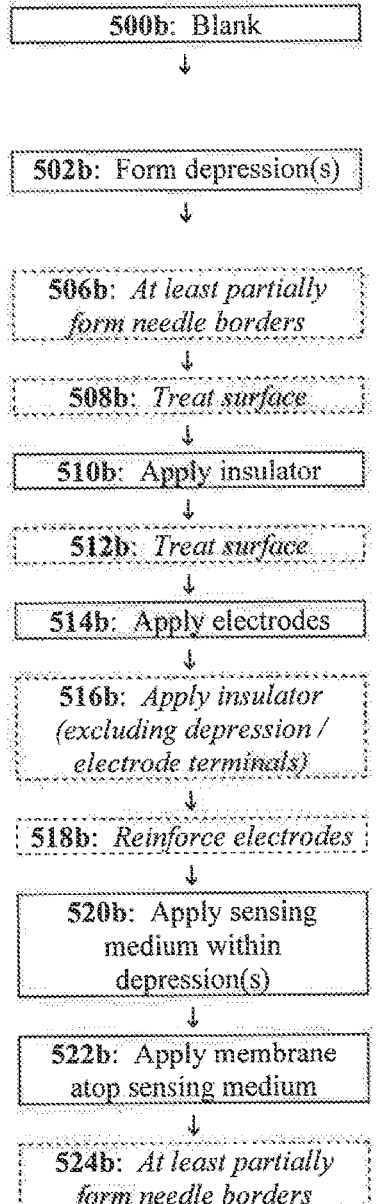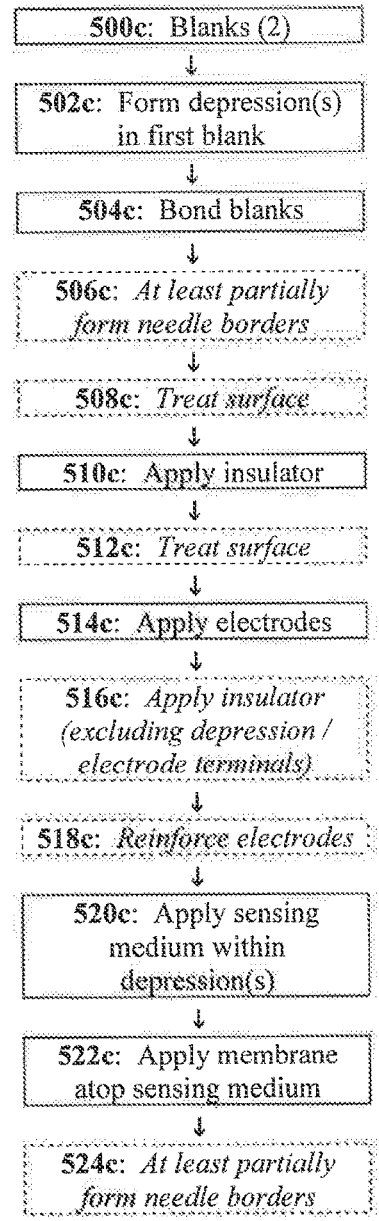

NEEDLES FOR MEASUREMENT OF BODY FLUID ANALYTES SUCH AS GLUCOSE

CROSS-REFERENCE TO RELATED APPLICATION(S)

This application is a U.S. National Phase Patent Application and claims priority to and the benefit of International Application Number PCT/US2019/064215, filed on Dec. 3, 2019, which claims priority to and the benefit of U.S. Provisional Patent Application No. 62/774,505, filed on Dec. 3, 2018, the entire contents of both of which are incorporated herein by reference.

FIELD OF THE INVENTION

The invention relates generally to measurement of analytes in body fluids (e.g., glucose in blood). The invention more particularly relates to compact (and ideally wearable) sensors for measurement of blood analytes. More particularly still, the invention relates to means for probing the body for the purpose of accessing body fluids for analyte measurement, as well as methods for making and using such probing means.

BACKGROUND OF THE INVENTION

Recent years have seen increased interest in wearable sensors for analytes in body fluids, e.g., blood glucose, because such sensors might greatly ease analyte measurement. This is particularly so where analytes are to be continuously (or at least frequently) measured, such as where diabetics need to frequently monitor their blood glucose levels. The reader is directed to US published patent applications 20180153520; 20170185284; 20170173261; 20170164878; 20160317070; 20110098599; 20100004522; 20050054907; 20090264720; 20030143746 for further background.

Analyte measurement methods can be categorized as invasive, that is, they require entry into the body or a body cavity (as where a probe is used to percutaneously access body fluid), or noninvasive. Invasive methods have traditionally used a probe in the form of a needle, but there has been limited interest in needle-based wearable analyte sensors because of recognized difficulties in designing and manufacturing a sufficiently compact and reliable needle-based system. Problems particularly arise with cost-effective manufacture of small and structurally robust needles. Very small needles are desired to reduce sensor size and minimize user sensation (particularly pain), but most methods of manufacturing "microneedles" produce needles of silicon (via conventional silicon micromachining or use of structural lithography resists, e.g., SU-8 photoresists), or plastic needles (via micromolding methods). Unfortunately, most silicon and plastic needles are not structurally robust, thus requiring larger dimensions, and/or are not biocompatible. Thus, wearable analyte sensor development has largely attempted to use noninvasive means for percutaneously probing the body to obtain measurements, e.g., spectroscopic, iontophoretic, sonophoretic, or similar methods for sensing analytes. Because these methods have limited accuracy and precision, such noninvasive sensors have had limited success.

SUMMARY OF THE INVENTION

The invention, which is defined by the claims set forth at the end of this document, is directed to needles and needle manufacturing methods which at least partially alleviate the aforementioned problems. A basic understanding of some of the features of exemplary versions of the invention can be attained from a review of the following brief summary of the invention, with more details being provided elsewhere in this document. To assist in the reader's understanding, the following review refers to the accompanying drawings (which are briefly reviewed in the "Brief Description of the Drawings" section following this Summary section of this document).

Referring to the accompanying FIGS. 1a and 1b, an exemplary needle 100 extends from a needle mounting tab 102, and has a needle length L extending from a needle tail 104 (seen in FIG. 1a) to a needle tip 106, wherein L is preferably less than 3 mm; a needle thickness T between a needle front 108 and an opposing needle rear (not shown), wherein T is preferably less than 0.5 mm; and a needle width W along the needle length L between opposing needle sides 112 (each needle side 112 being between the needle front 108 and needle rear), wherein W is preferably less than 0.5 mm. As seen in FIG. 1b, three electrodes extend along the needle length L, a working electrode 114, a counter electrode 116, and a reference electrode 118. As discussed at greater length below, where the foundation/substrate 100s of the needle 100 is formed of electrically conductive material, its outer surface preferably bears an electrically nonconductive first surface layer 120 upon which the electrodes 114, 116, and 118 are formed so that the electrodes are electrically isolated from the electrically conductive material, and thus from each other. Each electrode 114, 116, and 118 extends from an electrode terminal 114$t$, 116$t$, and 118$t$ adjacent the needle tip 106 toward the needle tail 104, and onto the mounting tab 102, where the electrodes preferably enlarge in at least one direction to provide contact pads 114$p$, 116$p$, and 118$p$ of greater area to which electrical connections can be made, and/or from which electrical measurements can so be taken. As seen in FIG. 1c, when the needle 100 is prepared for analyte measurement, a sensing medium 122 may be provided on a portion of the outer surface of the needle 100 over the electrode terminals 114$t$, 116$t$, and 118$t$ (these terminals being visible in FIG. 1b but not FIG. 1c), with the sensing medium 122 being configured to generate an electrical response measurable via the electrodes 114, 116, and 118 (in particular via their contact pads 114$p$, 116$p$, and 118$p$) when the sensing medium 122 is exposed to a selected analyte (e.g., glucose). The sensing medium 122 is preferably situated within a depression 124 (FIGS. 1a and 1b) indented within the outer surface of the needle 100, wherein the electrode terminals 114$t$, 116$t$, and 118$t$ are also situated within the depression 124. The electrodes 114, 116, and 118 are preferably covered by an electrically nonconductive second surface layer 126 between the depression 124 (and any sensing medium 122 therein) and the needle tail 104 so that these lengths of the electrodes are electrically isolated from body fluids when the needle 100 is inserted within a body.

To use the needle 100, the sensing medium 122 (FIG. 1c) is installed atop some or all electrodes, and if necessary or desired, a membrane 128 may be situated atop the sensing medium 122 to contain/constrain the medium 122 (if necessary), and/or to restrict exposure of the sensing medium 122 only to desired substances (e.g., where glucose is the analyte of interest, the is membrane may preferentially pass glucose, and perhaps oxygen as well). The needle 100 is thereafter inserted within a body, and the electrical response of the sensing medium 122 to exposure to the analyte may be measured from the electrodes 114, 116, and 118 (in particular from their contact pads 114*p*, 116*p*, and 118*p*).

For cost-effective manufacture, multiple needles 100 are preferably produced simultaneously (or nearly so) from a needle blank 200 (FIG. 2) made of a chosen needle substrate material, e.g., stainless steel. The needle blank 200 may take the form of a wafer, allowing manufacturing steps to be performed by use of wafer handling systems used in semiconductor production. Multiple needle templates 100*s* that is, needles consisting solely of the chosen needle substrate material, prior to addition of the aforementioned surface layers 120 and 126, electrodes 114, 116, and 118, sensing medium 122, etc.—may be formed in a single needle blank 200. Each needle template 100*s* preferably remains fixed to the needle blank 200 during at least some of the manufacturing steps (addition of the first surface layer 120, addition of the electrodes 114, 116, and 118, addition of the second surface layer 120, etc.) whereby the needle templates 100*s* can undergo simultaneous processing toward completed needles 100. The completed needles 100 may then be broken or otherwise removed from the needle blank 200 for final processing (if needed) and for use.

The depressions 124 within the needles 100, wherein the sensing medium 122 is situated, may be formed within the insulating second surface layer 126 (as best seen in FIG. 1*b*), or as suggested by the alternative exemplary needle 300 of FIG. 3, the depressions 324 may be formed directly in the needle blank 200 (more particularly, in the needle templates within the blank 200, with such a needle template being shown in FIG. 3 at 300*s*). When the depressions 324 are formed in the needle blank, they may be formed by milling a depression 324 within the thickness of each needle template 300*s* within the needle blank, as by use of laser skiving. FIG. 3 illustrates an exemplary needle 300 resulting from a fully-processed needle template 300*s* of such a needle blank. Alternatively, as suggested by the alternative exemplary needle 400 of FIG. 4, the needle blank (and the needle templates therein) may be formed by bonding a first needle blank layer 400*a* to a second needle blank layer 400*b*, wherein the depressions 424 are formed as through-holes extending through the first needle blank layer 400*a* and terminating and bottoming out at the second needle blank layer 400*b*. Regardless of whether the depressions are formed by cutting them into a blank (as in FIG. 3) or within a first blank layer bonded to another blank layer (as in FIG. 4), the first surface layer (320 in FIG. 3, 420 in FIG. 4) may thereafter be applied to the resulting needle blank, including within the depressions 324/424 of the needle templates within the needle blank. The electrodes 314/414, 316/416, and 318/418 may then be formed atop the first surface layer 320/420, with each needle template 300*s* and 400*a*/400*b* bearing a set of electrodes, and with their electrode terminals being situated within the depressions 324/424. The electrodes are preferably applied using photolithographic methods or wet etching, wherein the applied electrodes have borders conforming to apertures in a mask which is situated adjacent the first surface layer while the apertures are formed. The insulating second surface layer 326/426 can then be applied atop the electrodes 314/414, 316/416, and 318/418 and the first surface layer 320/420 outside the depression 324/424, whereby the electrodes are isolated to conductive communication with any sensing medium within the depression 324/424.

Where the depressions 124 are instead formed within the insulating second surface layer 126 (as in FIGS. 1*a*-1*c*), the first surface layer 120 is applied to the needle templates 100*s* of a needle blank 200, and the electrodes 114, 116, and 118 are then formed atop the first surface layer 120 (again with each needle template 100*s* within the blank having a set of electrodes 114, 116, and 118 formed thereon). The second surface layer 126 is then provided atop the electrodes 114, 116, and 118 save for at the electrode terminals 114*t*, 116*t*, and 118*t*, thereby forming the depressions 124 within the second surface layer 126 atop the outer surfaces of the needles 100 and above their electrode terminals 114*t*, 116*t*, and 118*t*. This is preferably done by first applying the second surface layer 126 atop the electrodes 114, 116, and 118 and their electrode terminals 114*t*, 116*t*, and 118*t*, and then removing the second surface layer 126 atop the electrode terminals 114*t*, 116*t*, and 118*t*, as by using a photoimageable second surface layer 126 which is exposed atop the terminals and then removed to form the depression 124. The resulting needles 100 may then be broken or otherwise removed from the blank 200 for use, either before or after their depressions 124 have been filled with sensing medium 122. Alternatively, each needle template's first surface layer 120, electrodes 114, 116, and 118, and second surface layer 126 may be peeled or otherwise removed from the needle template 100*s* to themselves define a needle, one which is flexible, and which may be wrapped about or otherwise adhered to the outer surface of a different carrier structure (e.g., a cannulated needle).

Further potential advantages, features, and objectives of the invention will be apparent from the remainder of this document in conjunction with the associated drawings.

BRIEF DESCRIPTION OF THE DRAWINGS

FIG. 5*a* depicts steps of an exemplary process for manufacturing needles 100 such as the one shown in FIGS. 1*a*-2.

FIG. 5*b* depicts steps of an exemplary process for manufacturing needles 300 such as the one shown in FIG. 3.

FIG. 5*c* depicts steps of an exemplary process for manufacturing needles 400 such as the one shown in FIG. 4.

DETAILED DESCRIPTION OF EXEMPLARY VERSIONS OF THE INVENTION

Needle Configuration

Figure 1A:
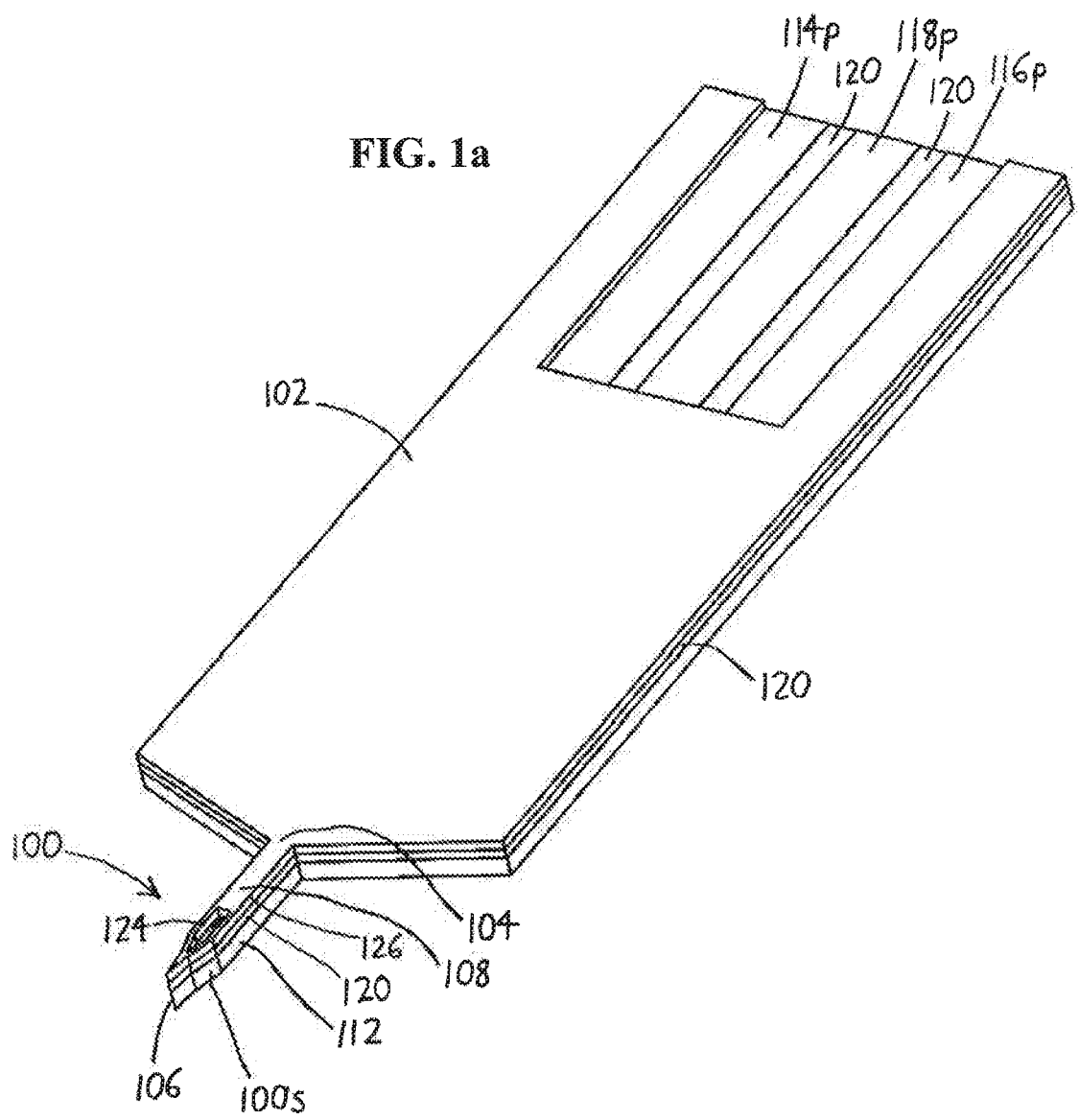
FIG. 1*a* is a perspective view of an exemplary needle 100 having a mounting tab 102 opposite its tip 106.
Figure 1B:
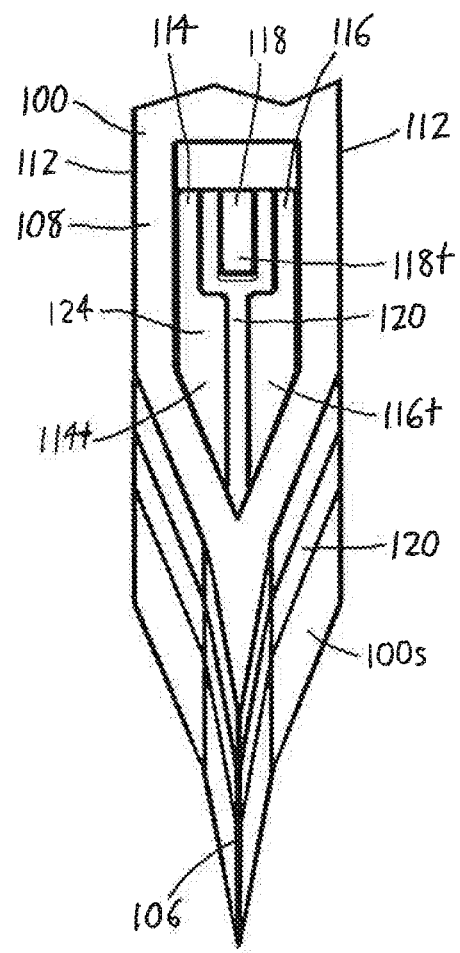
FIG. 1*b* is a detailed perspective view of the needle 100 of FIG. 1*a*, shown without the mounting tab 102, and further illustrating the electrodes 114, 116, and 118 atop the first surface layer 120 and within the depression 124 formed in the second surface layer 126.
Figure 1C:
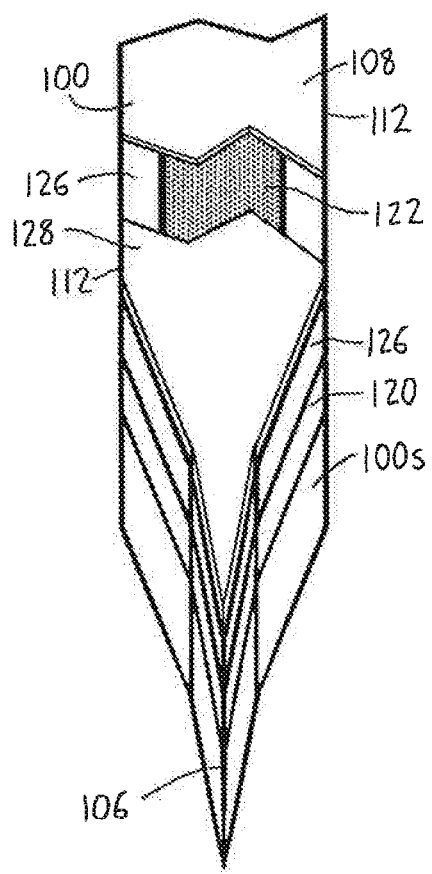
FIG. 1*c* is a perspective view of the needle 100 of FIG. 1*b*, shown with a sensing medium 122 applied within its depression 124, and with a membrane 128 applied over the sensing medium 122 (the membrane 128 being shown partially broken away to reveal the sensing medium 122).

FIG. 1*a* depicts an exemplary needle 100 in accordance with the invention. The needle 100 has a length L extending from a sharp needle tip 106 (shown in greater detail in FIG. 1b) to a needle tail 104, wherein a mounting tab 102 is joined to the needle tail 104; a thickness T between a needle front 108 and an opposing needle rear (not shown); and a needle width W extending between opposing needle sides 112, and which decreases as the tip 106 is approached. (W will is hereinafter be used to denote the average needle width along the midlength between the needle tip 106 and tail 104, that is, excluding any converging needle tip 106 and any diverging needle tail 104.) Electrodes 104, 106, and 108 extend along the front surface 108 of the needle 100 from terminals 114t, 116t, and 118t near the tip 106 to enlarged contact pads 114p, 116p, and 118p on the mounting tab 102, with such contact pads 114p, 116p, and 118p easing electrical connection to other components (not shown). The exemplary needle 100 is shown with a working electrode 114, a counter electrode 116, and a reference electrode 118, which may be used in a potentiostat, galvanostat, and/or other arrangement to produce an electrical signal (in conjunction with a sensing medium 122, shown in FIG. 1c) dependent on the concentration of the analyte of interest. Examples of such arrangements are described, for example, in US published patent applications 20190350502, 20190350504, 20190246961, 20190239778, 20180220967, and 20130199944, and in the references noted therein. As noted in these references, more or fewer electrodes may be used.

In use, at least some of the electrode terminals 114t, 116t, and 118t are coated with, or are otherwise in communication with, a sensing medium 122 (FIG. 1c) configured to respond in a measurable way to the presence of one or more analytes of interest, that is, one or more substances that are of interest for detection, quantification, or other analysis. Glucose will hereinafter be used to exemplify the analyte of interest for analysis, but sensing medium 122 can be chosen to detect other analytes, such as the "analytes," "features," and "characteristics" described in U.S. Pat. No. 9,492,109 to Bunge et al. and U.S. Pat. No. 9,687,182 to Bode et al. The sensing medium 122 can be any substance which provides a measurable response to the analyte of interest; for example, where glucose is the analyte of interest, a glucose oxidase enzyme or enzyme-containing substance might be used (with the enzyme-containing hydrogels of WO2019/113085A1 to Garner et al, and U.S. Pat. No. 9,549,697 to Valint Jr. et al. being examples). Such an enzyme, when exposed to glucose, produces a measurable electrical response which is dependent on glucose concentration. Thus, if the terminals 114t, 116t, and 118t are coated with an enzyme of this nature, and the needle 100 is then inserted through the skin until blood or interstitial fluid is encountered by the enzyme, the electrodes 104, 106, and 108 can be used to measure the response of the enzyme (e.g., via use of a potentiostat), and thereby measure glucose concentration. In a wearable device, the measurement results might then be wirelessly transmitted to a smartphone, smartwatch, or other computing device allowing processing, analysis, and/or display of the measurement results, if not done onboard the wearable device.

Sensing media 122 which are not electrically responsive, but which are instead chemically, spectroscopically, or otherwise responsive to the analyte(s) of interest, might instead (or also) be used (in which case the electrodes 104, 106, and 108 may not be included). However, such media 122 can pose greater challenges for response measurement while the needle 100 is inserted within a body owing to present technological difficulties and expense in providing means for measurement and transmission of response signals from such media 122. As an example, while it is possible to optically measure a spectroscopic response (such as change in reflectivity, absorption, emission, and/or other optical properties) in a sensing medium 122 on an inserted needle 100, it is difficult and expensive to do so owing to hurdles in providing one or more compact and optically efficient "light pipes" along the needle 100 which allow for illumination of, and/or light transmission from, the sensing medium 122. It is also or alternatively possible to measure such a spectroscopic response from outside the skin, but such measurements are difficult to accurately acquire with compact and low-power light emitters and sensors owing to optical signal interference by the intervening tissue. Similar challenges with signal measurement and transmission from an inserted needle 100 arise where the sensing medium 122 undergoes a change in chemical/physical properties which is not electrically measurable. Thus, some versions of the invention may not measure response signals from the sensing medium 122 while the needle 100 is inserted, and may instead insert the needle 100, perhaps dwell the needle 100 for a time sufficient to expose the sensing medium 122 to any analyte(s) of interest and provoke a corresponding response, and then withdraw the needle 100 so that the medium's response can be measured from the withdrawn needle 100 (for example, by detecting changes in color, fluorescence, etc.). In such versions of the invention, the electrodes 104, 106, and 108 need not be included because no electrical sensing medium 122 response may be measured.

To better protect and preserve the sensing medium 122 during needle insertion and/or needle storage, the sensing medium 122 is preferably provided within an elongated depression 124 defined in the needle front 108 near the needle tip 106. Where such a depression 124 is provided, the electrode terminals 114t, 116t, and 118t are situated within the depression 124 in communication with the sensing medium 122. Such a depression 124 is particularly useful where the sensing medium 122 is not entirely solid, and/or is soluble within body fluids, as the depression 124 can prevent or reduce migration of the sensing medium 122 from the electrode terminals (e.g., is smearing of the sensing medium 122 during insertion of the needle 100 into the body). With appropriate sensing media 122 for example, sensing media 122 that can be applied as a thin coating, and which are durable enough to tolerate possible rubbing/scraping during needle insertion and withdrawal no depression(s) 124 need be present, and the sensing medium 122 can simply coat a portion of one or more electrodes 104, 106, and 108. If necessary or desirable, a semipermeable membrane 128 might be provided over the sensing medium 122 (whether within a depression 124 or otherwise) to contain and protect it while allowing the analyte of interest (and any other desired substance) to pass the membrane 128 and access the sensing medium 122, and possibly to limit the amount of analyte accepted by the sensing medium 122 so as to adapt the response of the sensor provided by the electrodes 104, 106, and 108 and sensing medium 122 (e.g., to provide a linear response over a greater range of analyte concentrations). As examples, U.S. Pat. Nos. 5,882,494 and 5,777,060 to Van Antwerp, and US published patent applications 20180325436 and 20190307379, describe membranes and membrane materials suitable for use with glucose sensing media.

While the needle 100 can be made in various sizes having differing configurations, this document will assume a needle as shown in FIGS. 1a-4, and having the following dimensions (unless otherwise noted):

Overall needle width W: 0.2 mm

Overall needle thickness T: 0.2 mm
Overall needle length L: 1 mm (excluding mounting tab)
Overall needle depression width Wdep: 0.1 mm
Needle depression depth Ddep: 0.15 mm For sake of comparison, a typical hair from the head of an adult human has a diameter of approximately 0.8 mm. However, it should be understood that the needle can have different sizes and configurations. A preferred range of sizes follows:

Overall needle width W: 0.125-0.275 mm
Overall needle thickness T: 0.125-0.275 mm
Overall needle length L: 0.75-1.25 mm (excluding mounting tab)
Overall needle depression width Wdep: 0.05-0.150 mm
Needle depression depth Ddep: 0.01-0.25 mm The depression dimensions Wdep and Ddep are dependent on needle width W and thickness T. Following are preferred aspect ratios for the needle:

Ratio of needle width W to needle thickness T: 1-2
Ratio of needle thickness T to needle depression depth Ddep: greater than 1 but less than 2.5
Ratio of needle width W to needle depression width Wdep: greater than 1 but less than 5
Ratio of needle depression width Wdep to length of needle head (from needle tip to depression): greater than 0.2 but less than 5
Ratio of needle depression length to length of needle head (from needle tip to depression): greater than 0.2 but less than 5

The foregoing dimensions and proportions are based on needles 100 having needle substrates/templates 100s made of 316L FH stainless steel (SS). For SS needle templates 100s, it is also preferred that the walls and floor of the depression 124 always have a thickness of at least 0.04 mm or so for better structural robustness. Needle templates 100s may be made of other metals (or other materials, e.g., ceramic, plastic, or composite materials), with biocompatible materials having high strength and low brittleness, on the order of that of SS, being preferred. Needles made of materials other than SS might be dimensioned differently than stated above.

As other examples of variations in needle configuration, the needle front 108, needle rear, and needle sides 112 need not be discrete surfaces (i.e., need not be bounded by well-defined edges, and might be joined by continuous curves, and/or by beveled intermediate surfaces); the needle 100 may have different tip configurations (e.g., the tip 106 might be purely triangular, without discrete differently-sloped sections along its width, or might be a conical tip; the needle 100 may have several independent depressions 124, including depressions 124 on different (or multiple) faces of the needle 100; and the needle 100 may have more or fewer electrodes 104, 106, and 108, including electrodes 104, 106, and 108 which do not lead from depressions 124 (e.g., reference electrodes 118). As an example, the needle 100 depicted in FIG. la may have layers 120 and 126, a depression 124, and electrodes 104, 106, and 108 formed on its rear surface (not visible in the drawings) as well, thereby defining two sensor systems on the same needle. When in use, readings may be taken from each of the sensors (i.e., each of the electrode sets and their associated sensing media 122), and the agreement of the readings can provide an indication of their accuracy. Provided the readings agree to an acceptable extent, an average of the readings can be used as a representative reading. Or, where each sensor system utilizes a different sensing medium 122 for detection of a different analyte, the systems' readings can be used independently.

While no actuators for moving the needle 100 (or multiple needles 100) into (and also preferably out of) the skin are shown, it is expected that the needle 100 can be actuated in a manner similar to the needles used in wearable drug injection devices (with examples being shown in, for example, US published patent applications 20190022306, 20190022305, 20180250472, 20180193563, and 20170304557). The depression 124, electrodes 104, 106, and 108, and sensing medium 122 might even be implemented on the needles of such injection devices so that their needles can perform analysis of analytes as well as drug delivery. In this respect, drug delivery can also be performed by situating the drug(s) in one or more depressions 124 for release once the needle 100 is inserted. (Such depressions 124 are preferably independent of any depression(s) 124 containing the sensing medium.) The drug release may be via dissolution upon contact with body fluid (with the drug and/or a membrane thereover dissolving), via electrically-activated delivery (as by the electrode(s) to the drug-bearing depression(s) delivering a signal that dissolves or otherwise opens a membrane over the drug-containing depression, see, e.g., the aforementioned U.S. Pat. No. 9,492,109 to Bunge et al. and U.S. Pat. No. 9,687,182 to Bode et al.), or by other means. The needle 100 can therefore be utilized in a system wherein drug delivery is provided in response to analyte measurement. Nonetheless, it is not absolutely necessary that the needle 100 be coupled to an actuator for mechanically (or otherwise) moving the needle 100 into and out of the skin, and the needle 100 may simply be manually inserted within the skin until manually removed, as in U.S. Pat. No. 6,809,653 to Mann et al., U.S. Pat. No. 10,004,436 to Larvenz et al., and the prior patents cited in these references.

Cost-effective manufacture of the needle 100 in high volume can be challenging. The preferred needle manufacturing methods described below reduce these challenges.

Needle Manufacturing

Figure 2:
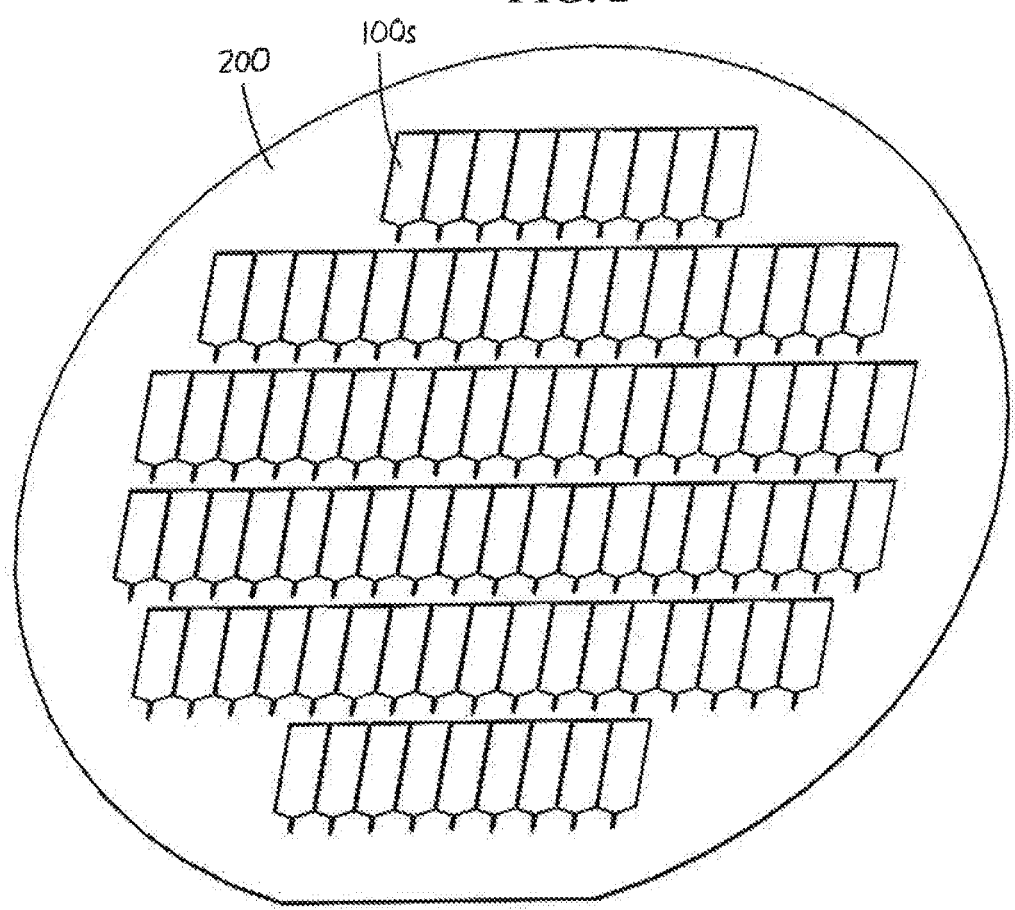
FIG. 2 illustrates a wafer 200 having several needle templates 100*s* formed therein, and from which several needles 100 as shown in FIG. 1 can be formed.

It is preferred that multiple needles 100 be produced simultaneously from a wafer or other sheet of stainless steel (or other substrate material) for sake of speed and efficiency, with FIG. 2 illustrating a wafer 200 bearing multiple needle templates 100s (that is, multiple needles formed substantially as shown in FIG. 1a, but prior to provision of the depressions, electrodes, sensing medium, etc. thereon). Throughout this document, the term "blank" will be used to refer to a sheet of any shape having dimensions sufficient to provide one or more (and preferably many) needle templates thereon. Thus, a "blank" may encompass only a single needle template 100s, or may encompass multiple needle templates 100s which are somehow connected.

Three particularly preferred methods for manufacturing needles are schematically depicted in the flowcharts of FIGS. 5a-5c; in all of these methods, it is assumed that multiple needles will be produced together in a blank such as the one shown in FIG. 2 at 200. In the method of FIG. 5a (relating particularly to the needle 100 of FIGS. 1a-1c), the depressions 124 are formed in an insulating layer (the aforementioned insulating second surface layer 126) used to isolate the electrodes 104, 106, and 108 from their surroundings. In the method of FIG. 5b (relating particularly to the needle 300 of FIG. 3), the depressions 324 are formed in the blank itself prior to forming the electrodes 314, 316, and 318 on the blank. In the method of FIG. 5c, a pair of blanks 400a and 400b is provided; the depressions 424 are formed as through-holes in one of the blanks 400a; and the blanks 400a and 400b are then bonded together in face-to-face abutment such that the bonded blank 400a bearing the through-holes defines the walls of the depressions 424, and the other blank 400b defines the floor of the depressions 424, with the electrodes 414, 416, and 418 thereafter being formed on the bonded blank 400. Each of the methods of FIGS. 5a-5c will now be discussed in greater detail. When referring to FIGS. 5a-5c, it is emphasized that the illustrated steps are exemplary and preferred, and not all illustrated steps are mandatory, with the steps illustrated in phantom/dashed-line boxes typically being more discretionary (though their degree of necessity may vary in dependence on the specifics of the materials and processes being used, and the results to be achieved). Further, the steps do not necessarily need to be performed in the illustrated order; for example, steps 524a, 524b, and 524c may be performed prior to steps 520a, 520b, and 520c, or even earlier (if performed at all). Additionally, it should be understood that similar steps in each of FIGS. 5a, 5b, and 5c for example, steps 506a, 506b, and 506c—can typically be performed similarly (again in dependence on the specifics of the materials and processes being used, and the results to be achieved). Thus, steps described for any one of FIGS. 5a, 5b, and 5c might be utilized in lieu of, or in addition to, steps described for any other of FIGS. 5a, 5b, and 5c.

Needle Manufacturing (FIG. 5a): Depression Formed in Insulating Layer on Needle Blank As noted above, FIG. 5a illustrates the steps of a process suitable for manufacture of needles such as that shown in FIGS. 1a-1c, wherein the depression 124 is formed within the surface layer 126 on the needle 100. Initially, in step 500a, a blank formed of a desired material is provided, preferably a blank formed of biocompatible metal, with a commercially available sheet of 8 mil thick (approximately 2 mm) 316L FH stainless steel (SS) being suitable. Materials other than SS might be used, e.g., titanium (Ti), but SS is preferred for its low cost and ready availability. It is particularly preferred to utilize a 10 cm circular SS wafer as the blank (as exemplified by the blank 200 in FIG. 2), as such a wafer allows many of the steps below to be at least partially automated via use of conventional wafer processing tools used in the semiconductor microfabrication field.

At step 506a, the needle borders (i.e., the needle sides and other boundaries between the needle front 108 and needle rear) of each needle 100 to be formed in the blank 200 may be partially formed in the blank 200 by use of laser (or other) cutting, preferably using a high power laser having dimensional accuracy of 0.025 mm or less. Alternatively, this step of partially forming the needle borders may be deferred until later, or may be partially performed here and further completed later, e.g., at step 524a (discussed below). Where multiple needles 100 are to be formed from the blank 200, the needle templates 100s are preferably arrayed across the blank 200 to yield the most possible needles 100 from a single blank 200. The needle borders are preferably only partially cut to leave breakaway tabs extending between each needle template 100s and the remainder of the blank 200, thereby removably joining each needle template 100s to the blank 200, so that the needles 100 may be handled and processed with the blank 200, and later broken away from the blank 200. These breakaway tabs may have any size, number, and location sufficient to maintain each needle 100 on the blank 200 during further processing; because they may be small and few where 316L FH SS is used as the blank material, they are not readily visible in FIG. 2, and thus are unlabeled. Step 506 need not be performed where the blank is only to provide a single needle, and is at least substantially configured as a needle template 100s (that is, where the blank is configured substantially as shown in FIG. 1a, save that it does not yet have the depression 124, electrodes 114, 116, and 118, and sensing medium 122). In this respect, the blank 200 and the needle templates 100s therein may have configurations which are substantially different from those shown in FIGS. 2 and 1a-1e; fur example, the blank of step 500a may take the form of a cannulated metal needle (i.e., the needle template may be a cannulated needle similar to a hypodermic needle), with at least some of the subsequent steps of FIG. 5a being performed on the cannulated needle to provide a needle which can both sense an analyte of interest and deliver a pharmaceutical or other substance in response to what is sensed.

At step 508a, if desired, the surfaces of the blank 200 (primarily the front surface, corresponding to the front surfaces 108 of the needles 100) may be treated as necessary or desired to prepare fur subsequent processing steps. Such treatment may include cleaning, passivation (i.e., coating or otherwise treating to reduce the chemical reactivity of the blank surfaces), and/or treatment to promote adhesion of matter applied to the blank surfaces in subsequent steps. Adhesion can be promoted by steps such as stripping/etching (e.g., using citric or other acids, hydrogen peroxide, or other caustics) and/or plasma treatment (e.g., via oxygen plasma), steps which also tend to clean/passivate the surfaces as well.

At step 510a, a biocompatible and electrically nonconductive first surface layer 120 is applied to at least the front surface of the blank 200 (and thus to the front surfaces 108 of the needles 100 formed in the blank 200). This insulating first layer 120 better ensures that the needle surfaces are electrically nonconductive, biocompatible, and smooth (smoothness being useful to reduce sensation by a user during needle insertion and/or withdrawal). The first surface layer 120 need not be applied if the needle templates 100s already sufficiently possess these qualities (e.g., where the blank 200 is formed of nonconductive material such as alumina). As an example, spin-coating can be used to apply a dielectric layer of polyimide to the blank 100 (preferably non-photoimageable polyimide if later processing steps involve optical lithography). Biocompatible organic polymers such as polyimide, parylene, and the like are preferred for the first surface layer 120 owing to their tendency to better smooth surface discontinuities in the blank 200, though other materials (e.g., silicon nitride, silicon dioxide, aluminum oxide) may be used instead (possibly requiring polishing of the blank surface at step 508a, and/or greater layer thickness, to avoid gaps/discontinuities). Where spin-coating is used to apply the first surface layer 120, it can be useful to defer the foregoing step of at least partially forming the needle borders (step 506a) until later (e.g., until step 524a), as the cuts in the blank 200 may interfere with rapid and uniform coating of the front surface of the blank 200. However, cuts or other discontinuities in the blank surface are of lesser concern if other coating methods (e.g., evaporation, sputtering, chemical vapor deposition, ion beam deposition) are used. The first surface layer 120 will not extend over the portion(s) of each needle boundary which will later be formed at the breakaway tabs when each needle 100 is broken from the blank 200, but this is not problematic so long as the later-formed electrodes 114, 116, and 118 remain electrically isolated from any conductive blank material, and so long as any surface discontinuities arising from breaking of tabs are tolerable.

If the insulating first surface layer 120 is applied without prior formation of the needle borders, it can be useful to delineate the desired needle borders in the insulating first surface layer 120 so they can be seen (either by eye or machine) in later processing steps. This can be done, for example, by applying an appropriate mask over the blank 200 (with slits corresponding to the needle borders), and then applying oxygen plasma treatment to etch away a desired amount of the first surface layer 120 (e.g., to remove approximately 40 nm of the first surface layer 120 at the needle borders).

At step 512a, if needed, the insulating first surface layer 120 may be treated to better promote adhesion of the later-formed electrodes 114, 116, and 118, and/or to otherwise better prepare the blank 200 for subsequent processing. As an example, some materials that may be used for the first surface layer 120 may not allow good adhesion of the electrodes without initial surface treatment of the first surface layer, at least near the regions where electrodes are to be applied, to roughen the surface or otherwise enhance its adhesion. Again, surface stripping/etching and/or plasma treatment can be used, generating nanoscale roughness on the insulating first surface layer, thereby increasing surface area and promoting electrode adhesion (and with the increased surface area beneficially increasing the surface area of any applied electrodes). Alternatively or additionally, an adhesion promoter such as an aminosilane might be applied.

In step 514a, the electrodes are applied atop the insulating first surface layer 120. While a variety of techniques can be used to form the electrodes 114, 116, and 118, such as the techniques discussed below with respect to steps 514b and 514c of FIGS. 5b and 5c, here lift-off or wet etching techniques are preferred. In an exemplary lift-off technique, a sacrificial layer is applied atop the insulating first surface layer 120; and the electrode pattern is then removed from the sacrificial layer until the first surface layer is revealed. Where the sacrificial material is a photoresist, removal may occur via light/radiation exposure through a mask having apertures in o the shape of the electrode pattern, followed by removal of the exposed photoresist via application of a developer solution, plasma stripping/ashing, or other means. Other techniques for removing the sacrificial material may alternatively or additionally be used, such as wet etching or plasma treatment of the sacrificial material through a mask having apertures in the shape of the electrode pattern. These steps leave the first surface layer 120 exposed through the sacrificial layer, in the pattern of the electrodes, whereby the sacrificial layer defines a mask through which the electrodes are to be applied. The blank 200 is then transferred to an appropriate metal deposition system (e.g., an electron beam evaporator or sputtering system) so that one or more metal adhesion layers (e.g., chromium or titanium) are deposited atop the sacrificial layer and the exposed first surface layer 120, followed by deposition of the primary conductor to be used for the electrodes (e.g., gold or platinum). Deposition of the metal adhesion layer(s) is preferred where the primary conductor for the electrodes has undesirably low adhesion to the first surface layer 120, otherwise it need not be included. An appropriate solvent is then applied to provide lift-off, with the solvent washing away the sacrificial layer (and any metal atop it), leaving the metal atop the insulating first surface layer 120 in the desired electrode pattern.

In an exemplary wet etching technique, the metal layer(s) can be directly sputtered atop the insulating first surface layer 120, at least over the region(s) where the electrodes are to be situated. A mask in the shape of the electrode pattern is applied atop the metal layer(s), and an appropriate etchant removes the unmasked metal from the first surface layer, leaving the masked metal atop the insulating first surface layer 120 in the form of the desired electrode pattern.

As an alternative to the foregoing techniques, the electrodes 114, 116, and 118 may be applied directly through a mask. Here a mask having openings defining the electrode pattern may be laser-cut into a substrate which can accommodate openings of the desired size (e.g., stainless steel or silicon). The mask is then aligned with, and clamped or otherwise affixed to, the blank 200. The masked blank 200 is placed in a suitable metal deposition system so that the electrodes 114, 116, and 118 may be formed on the blank's needles 100 through the mask.

In step 516a, an electrically nonconductive second surface layer 126 is applied atop the insulating first surface layer 120 and the electrodes 114, 116, and 118, save tor a region about the electrode terminals 114t, 116t, and 118t (this region defining the depression 124 into which the sensing medium 122 will be provided). This may be done by providing a mask over the desired depression region, applying the insulating second surface layer 126 over the mask and the unmasked portion of the blank 200, and then removing the mask to leave the depression 124. However, lithographic methods are particularly preferred for performing step 516a. Here the material for the second surface layer 126 is chosen to be a photoimageable dielectric material, such as SU-8, low temperature curable polyimide, silicone rubber, Fodel 6050 (DuPont Electronic Materials, Research Triangle Park, N.C., USA), epoxy phenol, or SINR 5170 (Shin-Etsu MicroSi is Inc., Phoenix, Ariz., USA). The material is spun or otherwise applied onto at least the front surface 108 of the blank 200, having a thickness equal to the desired depth of the depression 124, and is cured/dried. An appropriate mask either having an aperture in the shape of the desired depression 124, or having the shape of the desired depression 124, depending on whether the material is a positive or negative photoresist—is then situated over the electrode terminals 114t, 116t, and 118t, and is illuminated/irradiated. The second surface layer 126 at the depression region is then washed away with developer solution or otherwise removed, leaving the electrode terminals 114t, 116t, and 118t exposed atop the insulating first surface layer 120 within a depression 124 defined in the insulating second surface layer 126.

At step 518a, the exposed portions of the electrodes 114, 116, and 118, or at least their 2s electrode terminals 114t, 116t, and 118t, may be reinforced. At least the working electrode 114 may be electroplated, overprinted with conductive ink (Sonoplot, Middleton, Wis., USA), or otherwise dimensionally enhanced to increase surface area, thereby enhancing conductivity (improving sensor output) and/or providing further structural robustness.

At step 520a, a selected sensing medium 122 is deposited within the needle depressions 124, As noted previously, this step (as well as step 522a below) might alternatively be performed after the needles 100 are removed from the blank (at step 524a below).

At step 522a, a membrane 128 may be deposited over the sensing medium 122. An appropriate polymer for the membrane 128 may be dissolved in in organic solvent (such as tetrahydrofuran, dimethylformamide, acetone, or ethanol), and applied to at least the front surface of the blank 200 (and thus the front surfaces 108 of the needles 200 thereon) via any appropriate methods, such as drop, spray, dip or spin coating.

In step 524a, the needle borders may be formed beyond any extent already formed in step 506a. This may involve breaking or cutting the needles 100 from the blank 200 at their breakaway tabs, freeing the needles 100 from the blank 200 for subsequent use. If step 524a involves laser-cutting or other processes that might heat or otherwise degrade the sensing medium 122 and/or membrane 128, it might at least partially be performed earlier, for example, between steps 518a and 520a.

Step 526a is an optional step which may be performed where the final needles are to exclude the needle templates 100s of the blank 200, that is, where the needles are defined by the matter formed atop the blank 200, with such matter being peeled or otherwise removed from the is blank 200 to provide the final needles. The removed needles may then be applied to a desired substrate/needle template (e.g., following removal from the blank, a needle might be adhered to a preexisting needle/cannula or other probe), or might be used by themselves with a suitable injection system. In this case, the blank of step 500a and the surface treatment step 508a are preferably chosen to ease removal of the first insulating layer 120 from the blank 200; for example, the blank 200 may be formed of glass, and the surface treatment step 508a may involve depositing a soluble layer on the glass blank 200 which allows later detachment of the needles via lift-off processes.

Needle Manufacturing (FIG. 5b): Depression Formed in Needle Blank

In FIG. 5b, the depressions 324 of the needles 300 are formed in the needle blank itself (more particularly, in the needle template(s) within the blank), rather than being formed in one or more layers atop the blank.

In step 500b, a blank formed of an appropriate biocompatible material, e.g., a SS wafer as described above, is provided.

In steps 502b and 502e, the depression 324 and the borders of each needle 300 to be formed within the blank 200 are cut into the blank 200, preferably via laser cutting. The depression 324 may be produced by laser skiving (carving), removing material for some depth below the surface of the blank 200 and reducing the thickness of the skived area. Laser skiving can produce sloped depression sidewalls, which may be useful to ease later electrode deposition into the depression 324, but it can also result in a rough depression surface, which can complicate electrode deposition. Processing of the multilayer blank of FIG. 5c (described below) can avoid this issue, but at the expense of additional process steps. The depression 324 and needle borders may be cut in any order, or may be cut simultaneously. As in the process of FIG. 5a, the borders of the templates of the needles 300 are preferably not fully cut from the blank 200 at one or more locations, leaving the needles 300 connected to the blank 200 by breakaway tabs for ease of needle handling.

In step 508b, the surface of the blank 200 may be cleaned/passivated or otherwise treated, as in step 508a described above.

In step 510b, similarly to step 510a, a first insulating surface layer 320 is applied to at least the front surface of the blank (and at least the front surfaces 308 of the needles 300 formed therein). As an alternative to the spin-coated polyimide used in step 510a, parylene might be applied to the needles 300 via vapor phase deposition, preferably with a thickness of 0.01 mm or more. To assist parylene adhesion to the stainless steel (SS) surfaces of the templates of the needles 300, an adhesion promoter such as Silane A174 is preferably applied to the needle templates in step 508b prior to application of parylene in step 510b. Vapor phase deposition of parylene beneficially fully (or at least substantially) insulates all exposed needle surfaces, particularly at the depressed front needle side 308 and opposing rear needle side, and also tends to fill in surface discontinuities, resulting in a smoother surface.

In step 512b, the surface of the. blank 200 may be treated for better adhesion of subsequently-applied matter, as in step 512a described above. If the first surface layer 320 is formed of parylene, it can resist adherence of electrodes without such treatment. A suitable such treatment is to apply a surface stripper, e.g., Nano-Strip (KMG Chemicals, Ft. Worth, Tex., USA) for an extended period (e.g., 3 hours), followed by oxygen plasma treatment for a shorter period (e.g., 5 minutes). Both of these treatments enhance surface roughness and promote electrode adhesion. As in step 512a, an adhesion promoter might additionally or alternatively be applied.

In step 514b, the electrodes 314, 316, and 318 are applied to the needles 300 on the blank 200, The electrode formation of step 514b can be performed as in step 514a, or using any other suitable electrode formation methods. Platinum (Pt) is a preferred metal for use as electrodes on a parylene surface owing to its ability to suitably bond to parylene and most other polymeric surface layers, and owing to its electrochemical activity and biocompatibility. A thin layer of platinum can also usefully serve as an adhesion layer for a subsequently-applied different metal. A suitable thickness of a platinum electrode is approximately 200 nm; such a thickness preserves the enhanced electrode surface area arising from the surface treatment (as a thicker layer can "fill in" nanoscale valleys/gaps), and also better avoids thermal stress cracking of the parylene coating during deposition of the electrodes.

Figure 3:
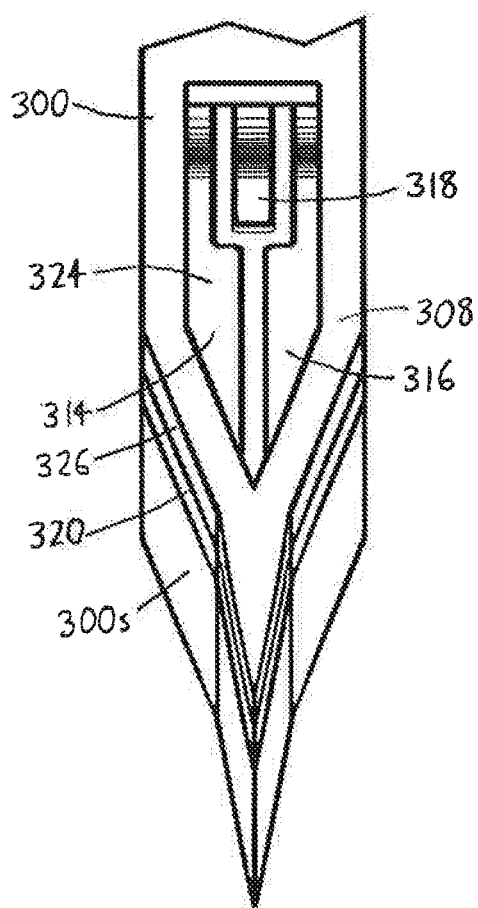
FIG. 3 is a perspective view of a second exemplary needle 300, wherein the needle's depression 324 is formed directly within its needle template/substrate 300*s*.

In the needle 300 of FIG. 3 and the method of FIG. 5b (as well as the needle 400 of FIG. 4 and the method of FIG. 5c), the transition of the electrodes 314, 316, and 318 from the upper surfaces 308 of the blank 200 and needles 300 into the needle depressions 324 can pose additional challenges for electrode formation. When using the lift-off technique described for step 514a, a dry film resist mask can be beneficial, as the dry film mask can "tent" over the needle depressions 324 and serve as a mask for the portions of the electrodes 314, 316, and 318 within the depressions 324. A preferred technique is to first apply the sacrificial layer to the blank 200, as by spin-coating is the blank 200 with a ~500 m layer of polydimethylglutarimide (PGMI), and then laminate a dry film resist (e.g., a 0.005 or 001 mm thick sheet of ADEX from DJ Microlaminates, Sudbury, Mass., USA) bearing the desired electrode pattern over the sacrificial layer. The resist is then exposed/irradiated, and developed to remove the exposed regions, revealing the sacrificial layer in the pattern of the electrodes 314, 316, and 318. The exposed sacrificial layer can then be removed, e.g., with 5-10 minutes of oxygen plasma treatment. The blank 200 is then transferred to a metal deposition system, and the electrodes 314, 316, and 318 are deposited through the mask. The blank 200 may then be immersed in a solvent bath, e.g., N-Methyl-2-pyrrolidone (NMP), with mild agitation, to remove the sacrificial layer and any stray electrode metal thereon, and to lift off the dry film mask. This leaves the metal electrodes 314, 316, and 318 on the needles 300, configured as dictated by the pattern on the dry film mask.

As an alternative or enhancement to use of the aforementioned electrode formation processes, any of the aforementioned processes can be used to form the electrodes 314, 316, and 318 within the depression 324 (and preferably just past the edges of the depression 324), and a conventional microfabrication technique such as lift-off can be used to form the sections of the electrodes 314, 316, and 318 outside the depression 324, with these sections overlapping the electrode sections extending from the edges of the depression 324. Using a lift-off technique, a patterned imaging resist is applied to the blank 200 and its needles 300; electrode metal is then deposited, adhering to the needles 300 where the resist was patterned to expose the needles 300; and the resist is then lifted off in a suitable solvent (e.g., NMP). The metal electrodes 314, 316, and 318 are left on the needles 300.

Following deposition of electrodes 314, 316, and 318, another surface coating 326 (e.g., parylene) might be applied to the needles 300, or selected portions thereof, in step 516b to insulate selected portions of the electrodes 314, 316, and 318 (for example, those portions outside the depression 324, or more generally away from any working, counter, and/or reference terminals 314t, 316t, and 318t which are to be left exposed to the sensing medium or to the environment).

Steps 518b (reinforcement of the electrodes 314, 316, and 318), 520b (application of the sensing medium to the depression 324), 522b (application of a membrane atop the sensing medium 322), and 524b (cutting needle borders) can all be performed similarly to steps 518a, 520a, 522a, and 524a in FIG. 5a.

Needle Manufacturing (FIG. 5c): Multilayer Bonded Blank

Figure 4:
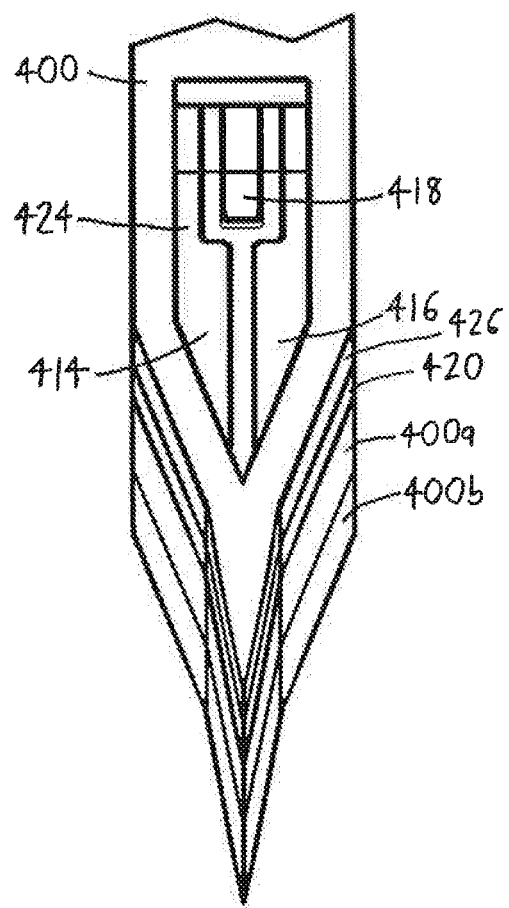
FIG. 4 is a perspective view of a third exemplary needle 400, wherein the needle's depression 424 is formed within one layer 400*a* within a bonded pair of layers 400*a* and 400*b* forming the needle template/substrate.

The method of FIG. 5c may be used to produce needles such as the needle 400 of FIG. 4. First and second blanks 400a and 400b—e.g., in the form of a circular wafer such as wafer 200 of FIG. 2—are provided (step 500c); the geometry of the depressions 424 is cut through the first blank 400a (step 502c); the cut first blank 400a is then bonded to the second blank 400b to form a needle blank 400 (step 504c); and the borders of the templates of the needles 400 are then each at least partially cut through the needle blank 400 about the depression 424 (step 506c). Thus, the depression walls are cut in the first blank 400a, and the floor of the depression 424 is defined by the second blank 400b. The first and second blanks 400a and 400b are preferably thinner in this method so that when they are bonded to form the needle blank 400, the needle blank 400 has roughly the desired needle thickness.

A particularly preferred method bonds the first and second blanks 400a and 400b in step 504c via gold-gold thermocompression bonding, wherein a gold layer is applied to a face of each of the first and second blanks 400a and 400b, and the gold layers of the blanks are then bonded together to affix the blanks and form the needle blank 400. In an exemplary method, a stainless steel (SS) first blank 400a is placed in a metal deposition system, e.g., a physical vapor deposition system such as an electron beam evaporator or sputtering system. Titanium (Ti), gold (Au), and titanium layers are consecutively deposited on one face of the first blank 400a (the "bonding face"), with each layer being relatively thin (e.g., approximately 100 nm thick). The first Ti layer applied to the bonding face of the first blank 400a serves as an adhesion layer for the subsequently-applied Au layer (as Au otherwise has poor adhesion to SS), and the second Ti layer applied over the Au layer serves as an adhesion layer for a photoresist (PR).

The photoresist is then applied to the outer Ti layer of the bonding face of the first blank 400a. In an exemplary method, spin-coating is used to apply a photoresist of ~0.01 mm thickness. Spaced discrete bonding areas are then patterned in the photoresist using standard lithographic techniques, e.g., ultraviolet light or other radiation is directed through apertures in a photomask to treat the illuminated/exposed bonding areas of the photoresist, so that the exposed bonding areas of the photoresist may thereafter be easily removed chemically or otherwise. As an example, an array of small circles, having diameters (and circle-to-circle spacing) of ~0.05 mm, might be formed in the photoresist on the bonding face. The exposed photoresist at the circular bonding areas (or bonding areas of other shapes) is then removed to uncover the outer Ti layer beneath, with these uncovered Ti areas being surrounded by the unexposed/unremoved PR. Ti etchant is then applied to remove the Ti at the bonding areas, uncovering the Au layer beneath, The bonding face of the first blank 400a then has uncovered Au bonding areas (e.g., the array of circles), with the Au bonding areas still being surrounded by the unexposed/unremoved photoresist.

The Au bonding areas on the bonding face of the first blank 400a—which, again, are thin (approximately 100 nm thick)—are then thickened by placing the first blank 400a in an electroplating Au bath. Further Au is electroplated onto the Au bonding areas, with the surrounding unexposed/unremoved photoresist serving as a sort of mold for the added Au. Au is added to the Au bonding areas until the holes in the unexposed/unremoved photoresist are filled in, or nearly so (e.g., until the Au bonding areas are 0.008 mm thick). The unexposed/unremoved. photoresist is then removed via stripping, ashing, or other conventional methods, leaving the Au bonding areas as "pillars" rising from the Au layer of the otherwise Ti/Au/Ti bonding face of the first blank 400a.

The depressions 424 are then cut entirely through the first blank 400a, preferably via laser cutting. Where the needle blank formed from the first and second blanks is to be used to produce multiple needles (as in FIG. 2), an appropriately-spaced array of depressions 424 can be cut into the first blank such that when the needle borders are subsequently cut about the depressions, the borders of one needle template do not extend over another needle template.

A stainless steel (SS) second blank 400b is placed in a metal deposition system, and a Ti layer is deposited on one thee (a "bonding face"), followed by an Au layer. Both layers are thin, e.g., approximately 100 nm thick, as with the first blank. The second blank 400b is then placed in the electroplating Au bath, and an Au layer of approximately 0.008 mm thickness is electroplated onto the bonding face.

The bonding faces of the first and second blanks 400a and 400b are then placed in abutment, and heated under compression (as by merely placing the blanks on a hot plate, or into an oven, with a suitable weight atop the blanks). The hot blanks 400a and 400b are then transferred to a bonding tool (e.g., a wafer bonding tool) and bonded using an Au—Au bonding recipe to generate the blank from which the needles 400 are to be cut.

Needle blanks made of bonded blanks/wafers can be prepared by any other suitable methods. As a simple example, a pair of stainless steel (SS) blanks, with one bearing the depression(s) cut through, can be joined using double-sided Kapton polyimide tape, and then bonded using a laminator or any other suitable bonding method.

Following bonding of the first and second blanks into a needle blank, steps 506c-524c can be performed as in either or both of FIGS. 5b and/or 5c, as described above.

Conclusion

Needles as described above can enable wearable analyte sensors having better measurement quality than wearable noninvasive analyte sensors. The use of a stainless steel or other structurally robust needle infrastructure allows needles having diameters in the tenths of millimeters. The use of laser cutting to form the needle infrastructure (and any depressions therein) significantly reduces cost in comparison to conventional micromachining techniques such as deep reactive ion etching used in silicon processing. Electrical isolation, needle smoothness, and biocompatibility can be promoted by addition of a surface coating, as by vapor deposition of parylene or polyimide. If necessary or desired, chemical surface stripping and oxygen plasma treatment of the surface coating can provide a reactive surface for direct deposition of one or more metallic electrodes, preferably via lithography, without using an adhesion layer. Such treatment of the surface coating can also provide a roughened surface so the deposited electrodes have nanoscale roughness, enhancing their electrochemical reactivity.

Throughout this document, where a measurement or other value is qualified by the term "approximately," "about," "nearly," "roughly," or the like for example, "approximately 0.2 mm" this can be regarded as referring to a variation of 10% from the noted value. Thus, as an example, "approximately 0.2 mm" can be regarded as encompassing dimensions between 0.1.8-0.22 mm.

Throughout this document, the various terms referring to orientation and/or position—e.g., "front" (as in "needle front") and "rear" (as in "needle rear")—are relative terms rather than absolute ones. In other words, it should be understood (for example) that the needle front being referred to may in fact be located at the rear of the needle depending on the overall orientation of the needle. Thus, terms of orientation and/or position should be regarded as words of convenience, rather than limiting terms.

The versions of the invention described above are merely exemplary, and the invention is not intended to be limited to these versions, Rather, the scope of rights to the invention is limited only by the claims set out below, and the invention encompasses all different versions that fall literally or equivalently within the scope of these claims.

What is claimed is:

1. A sensor comprising:
    a needle with an insertable portion that is entirely insertable into a body, the insertable portion having a tip, an end opposite the tip, a length measured from the tip to the end opposite the tip, a width measured in a direction perpendicular to the length that is less than the length, and a thickness measured in a direction perpendicular to both the length and the width, wherein the thickness at a distalmost free end of the tip is the same as the thickness of at least part of the end opposite the tip; and
    a plurality of electrodes each extending from the end opposite the tip towards the tip, wherein at least one of the electrodes has an electrode terminal with a portion closer to the tip than to the end opposite the tip that is attached laterally to the insertable portion.

2. The sensor of claim 1, further comprising a sensing medium configured to generate a response when exposed to one or more specific analytes, wherein the sensing medium covers at least a portion of the electrode terminal.

3. The sensor of claim 2, wherein the insertable portion of the needle defines a depression for holding the sensing medium.

4. The sensor of claim 3, wherein the electrode terminal is also located in the depression.

5. The sensor of claim 2, wherein one of the specific analytes comprises glucose.

6. The sensor of claim 2, wherein the needle comprises a biocompatible metal.

7. The sensor of claim 1, further comprising a mounting tab that extends from the end opposite the tip in a direction away from the tip, the mounting tab having a width greater than the width of the insertable portion, wherein each electrode extends from the insertable portion of the needle to the mounting tab.

8. The sensor of claim 1, wherein the electrodes are adhered laterally to the insertable portion of the needle.

9. The sensor of claim 1, wherein the electrodes are embedded into the insertable portion of the needle.

10. The sensor of claim 1, wherein the electrodes are inseparable from the insertion portion of the needle.

11. The sensor of claim 1, wherein the electrodes are integrally formed with the insertable portion of the needle during manufacture of the insertable portion.

12. The sensor of claim 1, wherein the insertable portion is solid at the end opposite the tip and is free from any recesses that extend axially towards the tip.

13. A method of manufacturing a sensor comprising a needle with an insertable portion that is entirely insertable into a body, the insertable portion having a tip, an end opposite the tip, a longitudinal axis extending between the tip and the end opposite the tip, a length measured from the tip to the end opposite the tip, a width measured in a direction perpendicular to the longitudinal axis that is less than the length, and a thickness measured in a direction perpendicular to both the length and the width, wherein the thickness at a distalmost free end of the tip is the same as the thickness of at least part of the end opposite the tip, and a plurality of electrodes each extending from the end opposite the tip towards the tip, wherein at least one of the electrodes has an electrode terminal with a portion closer to the tip than to the end opposite the tip, the method comprising:
    forming a first part of the insertable portion of the needle; and
    applying the electrodes laterally to the first part of the insertable portion of the needle in a direction transverse to the longitudinal axis.

14. The method of claim 13, wherein applying the electrodes laterally to the first part of the insertable portion of the needle comprises adhering the electrodes from a lateral direction onto the first part of the insertable portion of the needle.

15. The method of claim 13, wherein forming the first part of the insertable portion of the needle comprises forming a first insulating layer, and wherein applying the electrodes comprises applying the electrodes on the first insulating layer.

16. The method of claim 13, wherein a depression is formed in the first part of the insertable portion of the needle prior to applying the electrodes, and wherein the electrodes are applied such that the electrode terminal is located in the depression.

17. The method of claim 13, further comprising reinforcing at least some portions of the plurality of electrodes to enhance conductivity and/or increase structural robustness of the at least some portions of the electrodes.

18. A deposition method of manufacturing a sensor comprising a needle with an insertable portion that is entirely insertable into a body, the insertable portion having a tip, an end opposite the tip, a longitudinal axis extending between the tip and the end opposite the tip, a length measured from the tip to the end opposite the tip, and a width measured in a direction perpendicular to the longitudinal axis that is less than the length, and a plurality of electrodes each extending from the end opposite the tip towards the tip, wherein at least one of the electrodes has an electrode terminal with a first portion closer to the tip than to the end opposite the tip, the method comprising:

depositing a first insulating layer of the insertable portion of the needle;

applying the electrodes laterally onto the first insulating layer of the insertable portion of the needle in a direction transverse to the longitudinal axis via metal deposition; and depositing a second insulating layer over only part of the electrodes without covering a first region comprising at least the first portion of the electrode terminal of the at least one electrode by masking one of the first region or portions of the electrodes excluding the first region.

19. The method of claim 18, wherein the depositing of the second insulating layer comprises depositing the second insulating layer over the first portion of the electrode terminal and then forming a depression to expose at least the first portion.

20. The method of claim 18, further comprising reinforcing at least some portions of the plurality of electrodes that are not covered by the second insulating layer to enhance conductivity and/or increase structural robustness of the at least some portions of the electrodes.

\* \* \* \* \*